US011189361B2

(12) United States Patent
Utro et al.

(10) Patent No.: US 11,189,361 B2
(45) Date of Patent: Nov. 30, 2021

(54) FUNCTIONAL ANALYSIS OF TIME-SERIES PHYLOGENETIC TUMOR EVOLUTION TREE

(71) Applicant: INTERNATIONAL BUSINESS MACHINES CORPORATION, Armonk, NY (US)

(72) Inventors: Filippo Utro, Pleasantville, NY (US); Kahn Rhrissorrakrai, Woodside, NY (US); Chaya Levovitz, New York, NY (US); Laxmi Parida, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 757 days.

(21) Appl. No.: 16/022,088

(22) Filed: Jun. 28, 2018

(65) Prior Publication Data
US 2020/0004925 A1    Jan. 2, 2020

(51) Int. Cl.
*G16B 10/00* (2019.01)
*G16H 50/20* (2018.01)
*G16B 40/00* (2019.01)

(52) U.S. Cl.
CPC .......... *G16B 10/00* (2019.02); *G16B 40/00* (2019.02); *G16H 50/20* (2018.01)

(58) Field of Classification Search
None
See application file for complete search history.

(56) References Cited

U.S. PATENT DOCUMENTS 7,917,306 B2   3/2011   Frumkin
9,340,774 B2   5/2016   Damelin
(Continued)

FOREIGN PATENT DOCUMENTS

WO    2014152990 A1    9/2014
WO    2017197351 A1    11/2017

OTHER PUBLICATIONS

Dang et al., "ClonEvol: clonal ordering and visualization in cancer sequencing", Annals of Oncology, 28, pp. 3076-3082, doi:10.1093/annonc/mdx517. 2017.
(Continued)

*Primary Examiner* — William C Trapanese
(74) *Attorney, Agent, or Firm* — Cantor Colburn LLP; Kristofer Haggerty

(57) ABSTRACT

A computer-implemented method includes determining, by a processor, from a time-series evolution tree comprising one or more clones at each of the plurality of time points, that the one or more clones are sensitive clones or resistant clones, wherein the time-series evolution tree is based on sequence data for a tumor from a subject at a plurality of time points, wherein each time point in the time-series evolution tree represents an event in the subject's cancer treatment, and wherein a clone is a collection of gene alterations; based at least in part on determining that the one or more clones that are the sensitive or resistant clones, determining, by the processor, a geneset composition of the one or more clones that are the sensitive or resistant clones; and based at least in part on determining the geneset composition, determining by the processor, a further treatment for the subject.

19 Claims, 6 Drawing Sheets

(56) References Cited

U.S. PATENT DOCUMENTS

| | | | |
|---|---|---|---|
| 9,569,586 | B2 | 2/2017 | Rubben |
| 2002/0198664 | A1 | 12/2002 | Shackney |
| 2005/0038609 | A1 | 2/2005 | Benner |
| 2009/0186024 | A1 | 7/2009 | Nevins |
| 2009/0292482 | A1 | 11/2009 | Frumkin |
| 2012/0158391 | A1* | 6/2012 | Vaske .................. G06F 16/2219 703/11 |
| 2013/0011393 | A1 | 1/2013 | Lancaster |
| 2013/0332083 | A1* | 12/2013 | Laar ..................... C12Q 1/6886 702/19 |
| 2015/0261912 | A1 | 9/2015 | Sanborn |
| 2016/0357902 | A1 | 12/2016 | Yasuda |
| 2017/0298441 | A1 | 10/2017 | Wu |
| 2017/0321281 | A1* | 11/2017 | Iavarone .............. C12Q 1/6886 |
| 2018/0001184 | A1 | 1/2018 | Tran |
| 2018/0080090 | A1 | 3/2018 | Faham |
| 2018/0100201 | A1* | 4/2018 | Garraway ............ C12Q 1/6886 |
| 2019/0106751 | A1 | 4/2019 | Zimmermann et al. |
| 2019/0249261 | A1 | 8/2019 | Dingli et al. |

OTHER PUBLICATIONS

Deshwar et al., "PhyloWGS: Reconstructing subclonal composition and evolution from whole-genome sequencing of tumors", Genome Biology, doi: 10.1186/s13059-015-0602-8, 2015.

Liang et al., "An Improved Binary Differential Evolution Algorithm to Infer Tumor Phylogenetic Trees", Biomed Research International, doi.org/10.1155/2017/5482750, 2017.

Roth et al., "PyClone: Statistical inference of clonal population structure in cancer", Nat Methods. Apr. 2014; 11(4):396-398. doi:10. 1038/nmeth.2883.

Satas et al., "Tumor phylogeny inference using tree-constained importance sampling", Bioinformatics, vol. 33, No. 14, pp. I152-I160. SciSearch. 2017.

List of IBM Patents or Patent Applications Treated as Related; Date Filed: Sep. 4, 2018, 2 pages.

Rhrissorrakrai et al., "Time-Series Phylogenetic Tumor Evolution Trees," U.S. Appl. No. 16/022,075, filed Jun. 28, 2018.

Utro et al., "Phylogenetic Tumor Evolution Trees With Distribution of Variants in Cell Populations," U.S. Appl. No. 16/120,630, filed Sep. 4, 2018.

Bozic et al., "Quantifying Clonal and Subclonal Passenger Mutations in Cancer Evolution." PLOS Computational Biology, DOI:10. 1371/journal.pcbi.1004731 Feb. 1, 2016, 1-19.

El-Kebir et al., "Reconstruction of clonal trees and tumor composition from multi-sample sequencing data." Bioinformatics, 31, 2015, i62-i70.

Jiang et al., "Assessing Intratumor Heterogeneity and Tracking Longitudinal and Spatial Clonal Evolutionary History by Next-Generation Sequencing." Proceedings of the National Academy of Sciences of the United States of America 113.37 (2016): E5528-E5537. PMC. Web. May 15, 2018.

Malikic et al., "Clonality inference in multiple tumor samples using phylogeny." Bioinformatics, vol. 31, Issue 9, May 1, 2015, pp. 1349-1356.

Manica et al., "Inferring clonal composition from multiple tumor biopsies," ARXIV, https://arxiv.org/abs/1701.07940. Jan. 2017.

Xia, L. et al.; "SVEngine: an efficient and versatile simulator of genome structural variations with features of cancer clonal evolution"; GigaScience, vol. 7, Issue No. 7; 2018; 12 pages.

* cited by examiner

FUNCTIONAL ANALYSIS OF TIME-SERIES PHYLOGENETIC TUMOR EVOLUTION TREE

BACKGROUND

The present invention generally relates to computing systems, and more specifically to the functional analysis of time-series phylogenetic tumor evolution trees.

Tumors include a plurality of distinct cell populations. Massively parallel sequencing allows for the detection of somatic variants that correspond to cellular subpopulations in tumors. Collections of somatic variants, such as single nucleotide polymorphisms (SNPs) or other variants, are referred to as clones. Phylogenetic clone trees thus represent evolutionary relationships among genetic cell lineages in the tumor.

SUMMARY

Embodiments of the present invention are directed to a computer-implemented method for determining a treatment for a subject with cancer. A non-limiting example of the computer-implemented method includes determining, by a processor, from a time-series evolution tree comprising one or more clones at each of the plurality of time points, that the one or more clones are sensitive clones or resistant clones, wherein sensitive clones terminate in response to events in the subject's cancer treatment, and resistant clones survive, appear, or divide in response to events in the subject's cancer treatment, wherein the time-series evolution tree is based on sequence data for a tumor from a subject at a plurality of time points, wherein each time point in the time-series evolution tree represents an event in the subject's cancer treatment, and wherein a clone is a collection of gene alterations; based at least in part on determining that the one or more clones that are the sensitive or resistant clones, determining, by the processor, a geneset composition of the one or more clones that are the sensitive or resistant clones; and based at least in part on determining the geneset composition, determining by the processor, a further treatment for the subject.

Embodiments of the present invention are directed to computer program product for generating a cancer treatment. The computer program product includes a computer readable storage medium having program instructions embodied therewith. The program instructions are executable by a processor to cause the processor to perform a method. A non-limiting example of the system includes a computer readable storage medium having program instructions embodied therewith, the program instructions executable by a processor to cause the processor to perform operations. The operations include providing, based on sequence data for a tumor from a subject at a plurality of time points, a time-series tumor evolution tree, the evolution tree comprising one or more clones at each of the plurality of time points, wherein each time point in the evolution tree represents an event in the subject's cancer treatment, and wherein a clone is a collection of gene alterations; determining, by a processor, that the one or more clones are sensitive clones or resistant clones, wherein sensitive clones terminate in response to events in the subject's cancer treatment, and resistant clones survive, appear, or divide in response to events in the subject's cancer treatment; in response to the determination of the one or more clones that are the sensitive or resistant clones, determining, by the processor, a geneset composition of the one or more clones that are the sensitive or resistant clones; and in response to the determination of the geneset composition, determining by the processor, a further treatment for the subject.

Embodiments of the invention are directed to a system for cancer treatment. A non-limiting example of the system includes a processor; and a computer readable storage medium storing comprising executable instructions that, when executed by the processor, cause the processor to perform operations. The operations include providing, based on sequence data for a tumor from a subject at a plurality of time points, a time-series tumor evolution tree, the evolution tree comprising one or more clones at each of the plurality of time points, wherein each time point in the evolution tree represents an event in the subject's cancer treatment, and wherein a clone is a collection of gene alterations; determining, by a processor, that the one or more clones are sensitive clones or resistant clones, wherein sensitive clones terminate in response to events in the subject's cancer treatment, and resistant clones survive, appear, or divide in response to events in the subject's cancer treatment; in response to the determination of the one or more clones that are the sensitive or resistant clones, determining, by the processor, a geneset composition of the one or more clones that are the sensitive or resistant clones; and in response to the determination of the geneset composition, determining by the processor, a further treatment for the subject.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
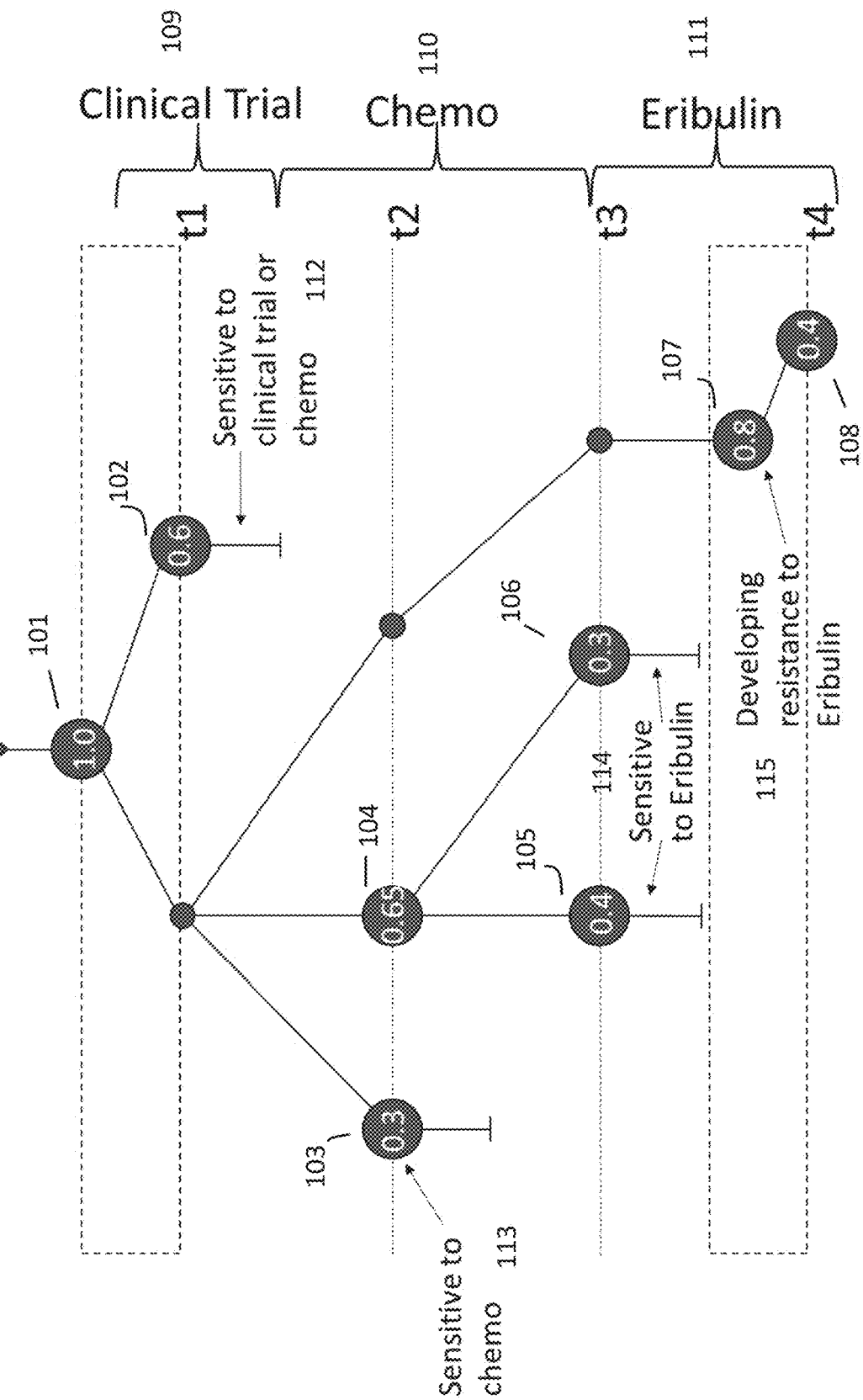
FIG. 1 depicts a time-series tumor evolution tree including a plurality of clones and with treatment responses indicated, wherein the frequency that a clone appears in the tumor at a given time point is shown by the value within the node according to embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the disclosed embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" can be understood to include any integer number greater than or equal to one, i.e. one, two, three, four, etc. The terms "a plurality" can be understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

Turning now to an overview of technologies that are more specifically relevant to aspects of the invention, phylogenetic clone trees have been constructed to represent evolutionary relationships among genetic cell lineages in a tumor. Typically, multiple samples from a patient's tumor are obtained and massively paralleled sequenced. Clustering of variants is used to infer the clonal evolution of the tumor. Various methods have been developed for the construction of phylogenetic clone trees such as PyClone, PhyloWGS, ClonEvol, and others.

Several definitions are provided. A variant is defined as a change in the most common genetic sequence. Variants can include single nucleotide variants (SNVs), which are single nucleotide variations, and indels, which are insertions/deletions, typically of 1 to 50 bases. SNVs and indels are collectively referred to as simple somatic variations (SSVs). The cancer cell fraction (CCF) of a variant is the fraction of sample with a particular variant. The variant allele frequency (VAF) is the relative frequency of a variant in a population, expressed as a fraction or percentage. The copy number variation (CNV) is when the number of copies of a particular gene varies.

As used herein, a clone is a collection of cells that are indistinguishable with respect to their SSVs. In other words, all the cells of a clone have the same set of SSVs.

As used herein a "geneset" is a biological pathway or collection of genes that results in a common phenotypic outcome. Exemplary genesets include microtubule inhibition pathways, DNA repair pathways, apoptosis pathways, and others.

An aspect that is missing from current phylogenetic evolution trees is the functional characterization of clonal evolution trees in the context of a patient's history. With one or more sequencing samples taken from a tumor at different times during a patient's treatment history, it is possible to construct trees that represent the evolution of the cancer over time, i.e., time-series clonal evolution trees. As the cancer ages, this dynamic system is consistently acquiring and losing alterations as it responds to environmental, immunological, and therapeutic perturbations, for example. Efforts to understand the evolution of the cancer are made more difficult as result of the typical intra-tumoral heterogeneity, where there are often multiple sub-clonal populations. Time-series clonal evolution trees permit the correlation of changes in clonal populations with respect to environmental stimuli. Clonal trees also naturally organize the thousands of somatic alterations that may or may not be present in a tumor, allowing the identification of genesets associated with environmental stimuli.

More particularly, the treatment of cancer is often predicated on the targeted attack of particular genesets or through the recruitment of the patient's immune system. However, over the course of treatment, these cancers, with their different sub-populations of cells, can possibly overcome the targeted treatment mechanism through selection of resistant clones, or the acquisition of new alterations that aid survival. Because there can be tens or hundreds of thousands of somatic mutations in a given cancer, the search space of the relevant dysfunctional genes is incredibly large. Time-series clonal trees can help to reduce the search space and facilitate the identification of genesets that can be implicated in the cancer's viability and used as potential targets.

Turning now to an overview of aspects of the invention, one or more embodiments of the invention address the above-described shortcomings of the prior art by providing a method to functionally characterize clonal evolution trees in the context of the patient's treatment history. It is thus possible to adjust the course of treatment to shift a non-responder to a responder, or a patient with acquired resistance to one that is once more responsive.

The above-described aspects of the invention address the shortcomings of the prior art by functionally characterizing time-series tumor evolution trees using identified genesets in the context of the patient's history, and using the identified genesets to guide treatment of the patient.

In a clonal birth-death time series tumor evolution tree, each node represents a collection of alterations at a given time point in the patient's treatment history. This collection of alterations is referred to as a clone, and for the set of alterations, two modes of analyses are performed.

Figure 3:
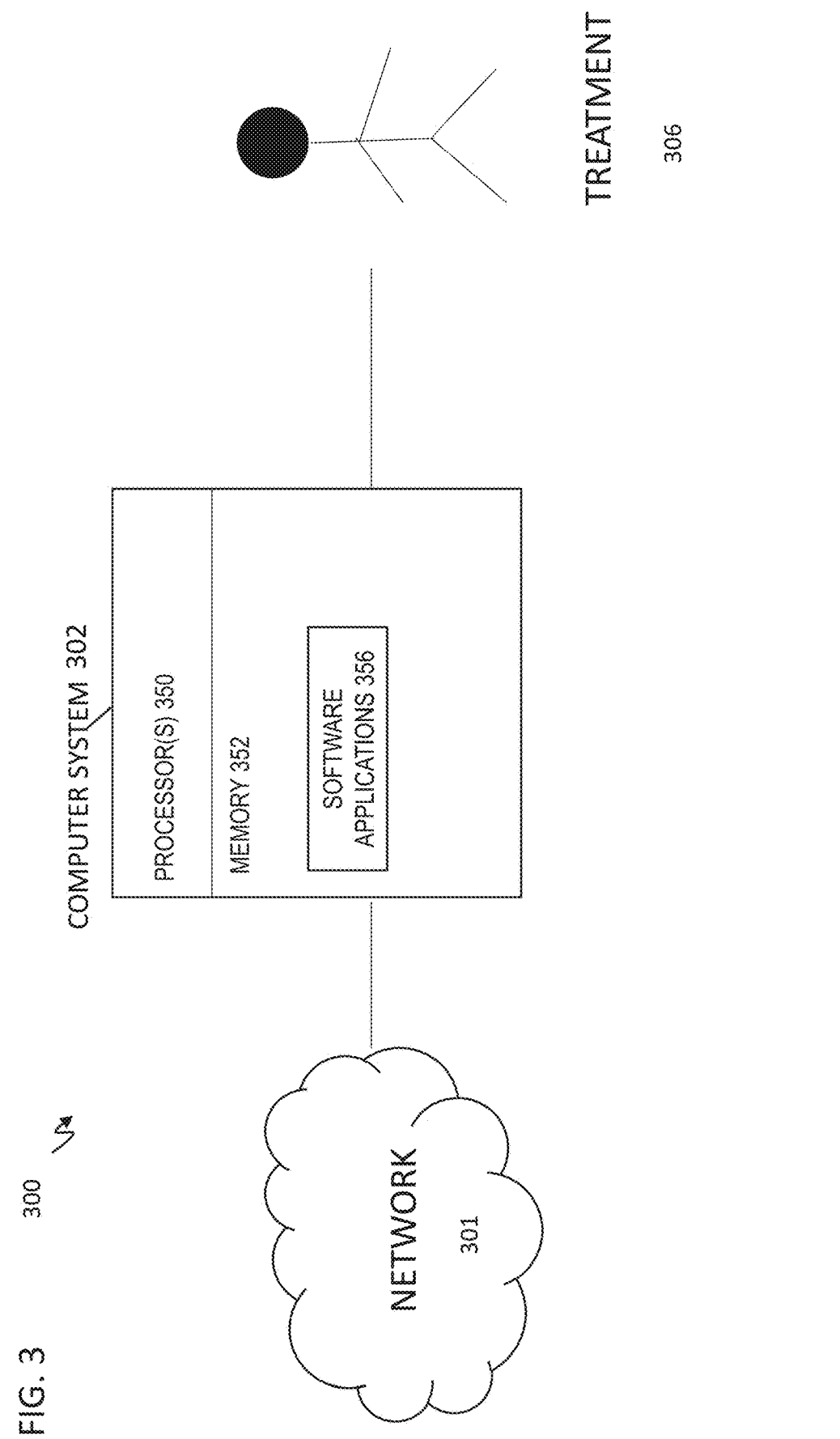
FIG. 3 illustrates a system for determining a cancer treatment according to embodiments of the present invention.

First, an analysis of the topology with respect to the patient's treatment history is made (e.g., by computer system 302 depicted in FIG. 3). FIG. 1 illustrates a time-series tumor evolution tree 100 with time point-specific clones 101-108, and with treatment responses 112-115 indicated. The frequency the clone appears in the tumor at a given time point (e.g., the VAF) is shown by the value within the node. A processor 350 executes a software application 356 (depicted in FIG. 3) to create the time-series tumor evolution tree 100 in FIG. 1.

Given the time series evolution tree 100, clones that terminate within or soon after a treatment is applied are considered as likely sensitive to the treatment. Clones that continue to survive, divide, or emerge during a treatment are considered to be likely resistant to the treatment. The sensitive and resistant response labels are determined by software applications 356 depicted in FIG. 3. With these phenotypic response labels, it is possible to apply a variety of supervised analyses, e.g., by a processor 350, on trees across many patients to identify consistent patterns of tree behaviors or clonal compositions. Thus, the treatment of a single patient can be guided by collective data obtained for a population of patients.

Second, a geneset analysis 400 is performed (e.g., by computer system 302 depicted in FIG. 3) whereby given a collection of alterations 403, i.e., a clone, in a time-series tree 401, it is determined by the processor 305 which geneset 405 is most likely to be affected and yield the resulting phenotype, e.g., resistant or sensitive. A non-limiting example of geneset analysis is to perform a Fisher's exact test (e.g., by the computer system 302) on the intersection between the set of genes in the clone and the clone's ancestors with those in the geneset of interest. By performing this analysis for each node in the tree, the time point at which a geneset is affected can be characterized. Once the geneset 405 has been identified, a further treatment 407 for the subject can then be determined by the processor 350, using a database 406.

The representation of the tumor mutational history described herein reduces the dimensionality of the search space allowing for signals to be discovered in an individual patient or across patients within a cohort that is not possible at individual mutation or gene level. This new representation of tumor evolution into a geneset space can then be used by machine learning and artificial intelligence methods (e.g., by software applications 356) that can determine and extract patterns from both a structured representation of this transformation and a visualization of the evolution, as in FIG. 2. The processor 350 executes the software application 356 (depicted in FIG. 3) to create the geneset representation 200 in FIG. 2. The geneset representation 200 also captures the biological reality that genes exist within pathways or molecular machines where there are often functional redundancies and multiple members of the pathway can be affected before a phenotype change is made. By understanding the affected pathways, the processor can determine a further treatment for the subject that directly or indirectly target the identified pathway. The clinician can then apply the treatment.

More specifically, using the patterning of when genesets become significantly represented, associations to the driving mechanisms of the cancer or the mechanisms of treatment response and resistance can be made. These mechanistic associations, determined by the software application 356, are used by the processor 350 to determine a further treatment for the subject.

Figure 2:
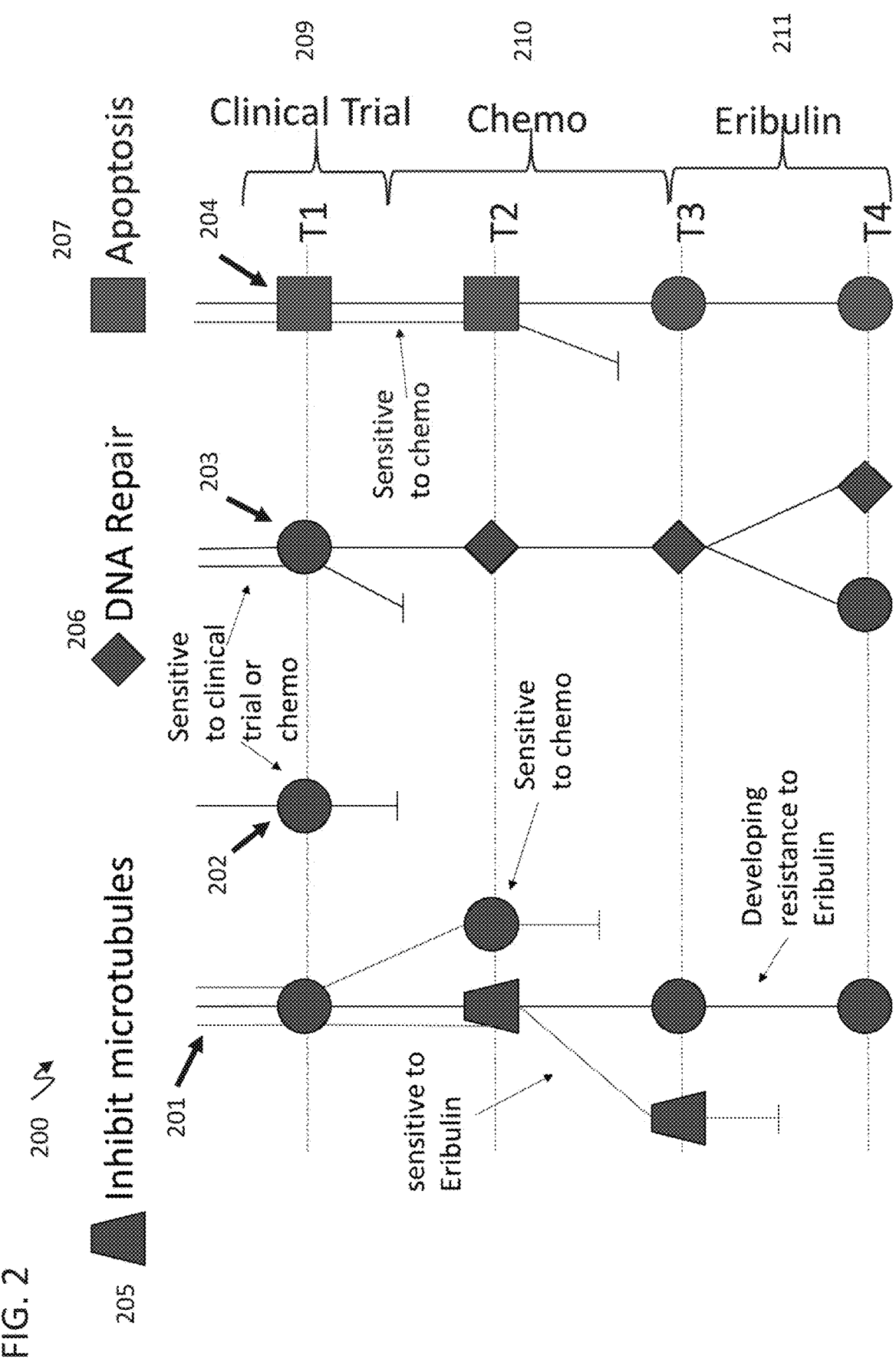
FIG. 2 depicts tumor evolution with time point-specific clones highlighted for the geneset that is affected according to embodiments of the invention.

For example, in FIG. 2, it was observed that for a given patient tumor sampled at four time points, certain clonal lineages 201-204 appear to have particular mechanisms 205-207 that arise as significant in response to treatments 209-211. The DNA repair pathway 206, for example, became most likely affected at time T2 210, potentially in response to the treatments given between times T1 209 and T2 210. With this information, the processor 350 can determine further treatments that target the DNA repair pathway mechanism to overcome the developing resistance. The microtubule inhibition pathway 205 was significantly mutated by time T2 210. This patient was then given eribulin, an inhibitor of microtubules at T3 211, and clones where that pathway was significantly mutated were sensitive to treatment and died. From this pattern, the processor 350 can learn that clones affecting microtubule inhibition should more likely be given eribulin. Similarly, for the apoptosis pathway 207, clones affecting the apoptosis pathway are sensitive to chemotherapy at T2 210, but were resistant to the clinical trial at T1 209.

In an aspect of the invention, a computer-implemented method by software applications 356 executed on processor 350 includes providing, based on sequence data for a tumor from a subject at a plurality of time points (such as, e.g., t1, t2, t3, t4), a time-series tumor evolution tree (such as, e.g., time-series tumor evolution tree 100), the time-series evolution tree including one or more clones (such as, e.g., clones 101-107) at each of the plurality of time points (e.g., 209-211), wherein each time point in the time-series evolution tree represents an event, e.g., chemotherapy, in the subject's cancer treatment, and wherein a clone is a collection of gene alterations (e.g., SSVs); determining, by a processor 350, that the one or more clones are sensitive clones or resistant clones, wherein sensitive clones terminate in response to events in the subject's cancer treatment, and resistant clones survive, appear, or divide in response to events in the subject's cancer treatment; in response to the determination of the one or more clones that are the sensitive or resistant clones, determining, by the processor 350, a geneset composition (e.g., geneset composition 205-207) of the one or more clones that are the sensitive or resistant clones; and in response to the determination of the geneset composition, determining by the processor 350, a further treatment for the subject. In an aspect, the subject is a human subject.

In an aspect of the invention, the subject's cancer treatment includes radiation therapy, surgery, chemotherapy, targeted therapy, hormone therapy, immunotherapy, stem cell transplant, or a combination including at least one of the foregoing.

A time-series tumor evolution tree (e.g., time-series tumor evolution tree 100) can be constructed (via software applications 356) by determining the SSVs for a tumor at a plurality of time points, using either CCF and/or the VAF for the SSVs to calculate time-resolved mutation frequencies for each SSV, and using the time-resolved mutation frequencies to construct the time-series tumor evolution tree, wherein each time point in the evolution tree represents an event in the subject's cancer treatment.

Sensitive and resistant clones are shown in the schematic of FIG. 1. As illustrated in FIG. 1, clone 103 is sensitive to the chemotherapy applied at time T2 110. That is, clone 103 terminates upon treatment. Thus, the target geneset for clone 103 can continue to be targeted with the same or a different therapy, as determined by the computer system 302 depicted in FIG. 3.

As also illustrated in FIG. 1, the clone 104 survived chemotherapy at T2 110 and also divided into clones 105, 106, thus clone 104 was a resistant clone, suggesting that a different strategy targeting a different geneset, such as eribulin treatment should be undertaken as determined by the computer system 302 depicted in FIG. 3. Eribulin treatment changed the resistant clone 104 into sensitive clones 105, 106 which terminated upon eribulin treatment.

Yet further in FIG. 1, the clone 107 appeared after eribulin treatment at T3 111, suggesting development of resistance to eribulin treatment as determined by computer 302. A different strategy targeting a different geneset should thus be undertaken as determined by the computer system 302 depicted in FIG. 3.

In an aspect of the invention, determining, by the processor 350, the geneset composition (such as, e.g., geneset composition 205-207) of the one or more clones that are the sensitive or resistant clones, includes performing, by the processor 350, a test to determine whether a geneset can be associated to a clone of interest. In an embodiment, the test is a Fisher's exact test on the significance of the size of intersection between members of a genset and a clone of interest. This detection enables characterizing the dynamics by which genesets may be affected over time. Genesets can be identified using publicly available tools such as the Molecular Signatures Database (MSigDB), Enrichr, GeneSCF, the Database for Annotation, Visualization and Integrated Discovery (DAVID), AmiGO 2, the Genomic region enrichment of annotations tool (GREAT), and others. In some implementations, these tools can be utilized, included, and/or integrated with software applications 356.

The method includes, in response to the determination of the geneset composition, determining by the processor 305, a further treatment for the subject 407. In an aspect of the invention, determining by the processor 305, a further treatment 407 for the subject, includes comparing, by the processor 305, the geneset composition 405 with a database 406 determined from a plurality of tumors from a plurality of subjects. The database 406 can include data from tens to thousands of subjects to allow the processor 305 to correlate specific genesets to further treatments. The processor 305 performs this correlation by correlating outcomes from treatments applied to the plurality of subjects such that projected treatment outcomes can be determined.

In another aspect of the invention, the further treatment determined by the processor 305 includes a signal transduction pathway inhibitor, an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination including one or more of the foregoing.

More specifically, further treatment determined by the processor 305 thus include signal transduction pathway inhibitors (e.g., ErbB inhibitors, EGFR inhibitors such as erlotinib), antimetabolites (e.g., 5-fluoro-uracil, methotrexate, fludarabine), antimicrotubule agents (e.g., vincristine, vinblastine, taxanes such as paclitaxel, docetaxel), an alkylating agent (e.g., cyclophosphamide, melphalan, biochoroethylnitrosurea, hydroxyurea), nitrogen mustards, (e.g., mechloethamine, melphan, chlorambucil, cyclophosphamide and Ifosfamide); nitrosoureas (e.g., carmustine, lomustine, semustine and streptozocin;), platinum agents (e.g., cisplatin, carboplatin, oxaliplatin, JM-216, C 1-973), anthracyclines (e.g., doxrubicin, daunorubicin), antibiotics (e.g., mitomycin, idarubicin, adriamycin, daunomycin), topoisomerase inhibitors (e.g., etoposide, camptothecins), alkyl sulfonates including busulfan; triazines (e.g., dacarbazine); ethyenimines (e.g., thiotepa and hexamethylmelamine); folic acid analogs (e.g., methotrexate); pyrimidine analogues (e.g., 5 fluorouracil, cytosine arabinoside); purine analogs (e.g., 6-mercaptopurine, 6-thioguanine); antitumor antibiotics (e.g., actinomycin D; bleomycin, mitomycin C and methramycin); hormones and hormone antagonists (e.g., tamoxifen, cortiosteroids), anti-angiogenic agents (bevacizumab, endostatin and angiostatin), immunotherapeutic agents (transfection with cytokines such as interleukin 2, interleukin 4 or granulocyte-macrophage colony stimulating factor), cell cycle signaling inhibitors (CDK2, CDK4, and CDK6 inhibitors) and any other cytotoxic agents, (e.g., estramustine phosphate, prednimustine).

For example, signal transduction inhibitors include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes. Growth factor receptor tyrosine kinases include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Tyrosine kinases, which are not growth factor receptor kinases are termed non-receptor tyrosine kinases. Non-receptor tyrosine kinases include cSrc, Lck, Fyn, Yes, Jak, cAbl, FAK (Focal adhesion kinase), Brutons tyrosine kinase, and Bcr-Abl.

Inhibitors of Serine/Threonine Kinases include MAP kinase cascade blockers which include blockers of Raf kinases (rack), Mitogen or Extracellular Regulated Kinase (MEKs), and Extracellular Regulated Kinases (ERKs); and the Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases.

Inhibitors of Phosphotidyl inositol-3 Kinase family members including blockers of PI3-kinase, ATM, DNA-PK, and Ku.

Inhibitors of Ras Oncogene include inhibitors of farnesyltransferase, geranyl-geranyl transferase, and CAAX proteases as well as anti-sense oligonucleotides, ribozymes and immunotherapy.

Alkylating agents alkylate molecules such as proteins, RNA and DNA and can covalently bind these molecules.

Alkylating agents can affect any point in the cell cycle and thus are known as cell cycle-independent drugs.

Antimetabolites impede DNA and RNA synthesis.

Anti-microtubule agents block cell division by preventing microtubule function.

In a specific aspect, as illustrated in FIG. 2, a clone is found to be significantly enriched for a pathways relating to microtubule formation 205 and that pathway arose as a resistant clone to prior therapies, then treatment with a microtubule inhibitor might be suggested if the molecular target of the therapy still falls within indication criteria.

The method can include administering the further treatment to the subject.

FIG. 3 depicts a system 300 according to embodiments of the invention. Network 301 and computer system 302 can be used to store and communicate sequence data for tumors from one or more subjects as well as time-series tumor evolution trees 303. Using the computer-implemented process, the time-series tumor evolution trees 303 is converted to a geneset 304. Also using the computer-implemented process, the identified geneset is used to make a treatment decision 305 which can then be administered to a patient. The computer system 302 includes one or more processors 350, memory 352, and one or more software applications 356 having computer-executable instructions to function as discussed herein. The processors 350 are configured to the execute computer-executable instructions of the software applications 356 as discussed herein. An individual 306 can be a patient, human, subject, etc., as discussed herein.

Figure 4:
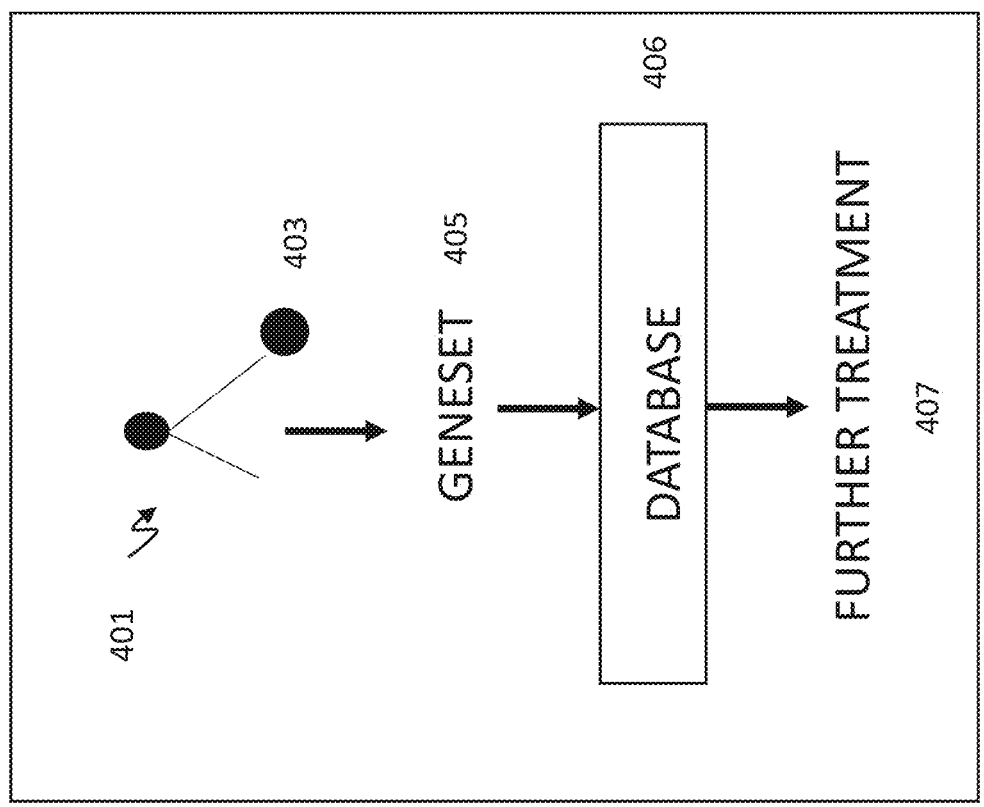
FIG. 4 illustrates a system for geneset analysis according to embodiments of the present invention.

FIG. 4 is a system for geneset analysis 400 according to embodiments of the present invention. From a collection of alterations 403, i.e., a clone, in a time-series tree 401, it is determined, by the processor 305, which geneset 405 is most likely to be affected and yield the resulting phenotype, e.g., resistant or sensitive. Once the geneset 405 has been identified, a further treatment 407 for the subject can then be determined by the processor 350, using a database 406.

Figure 5:
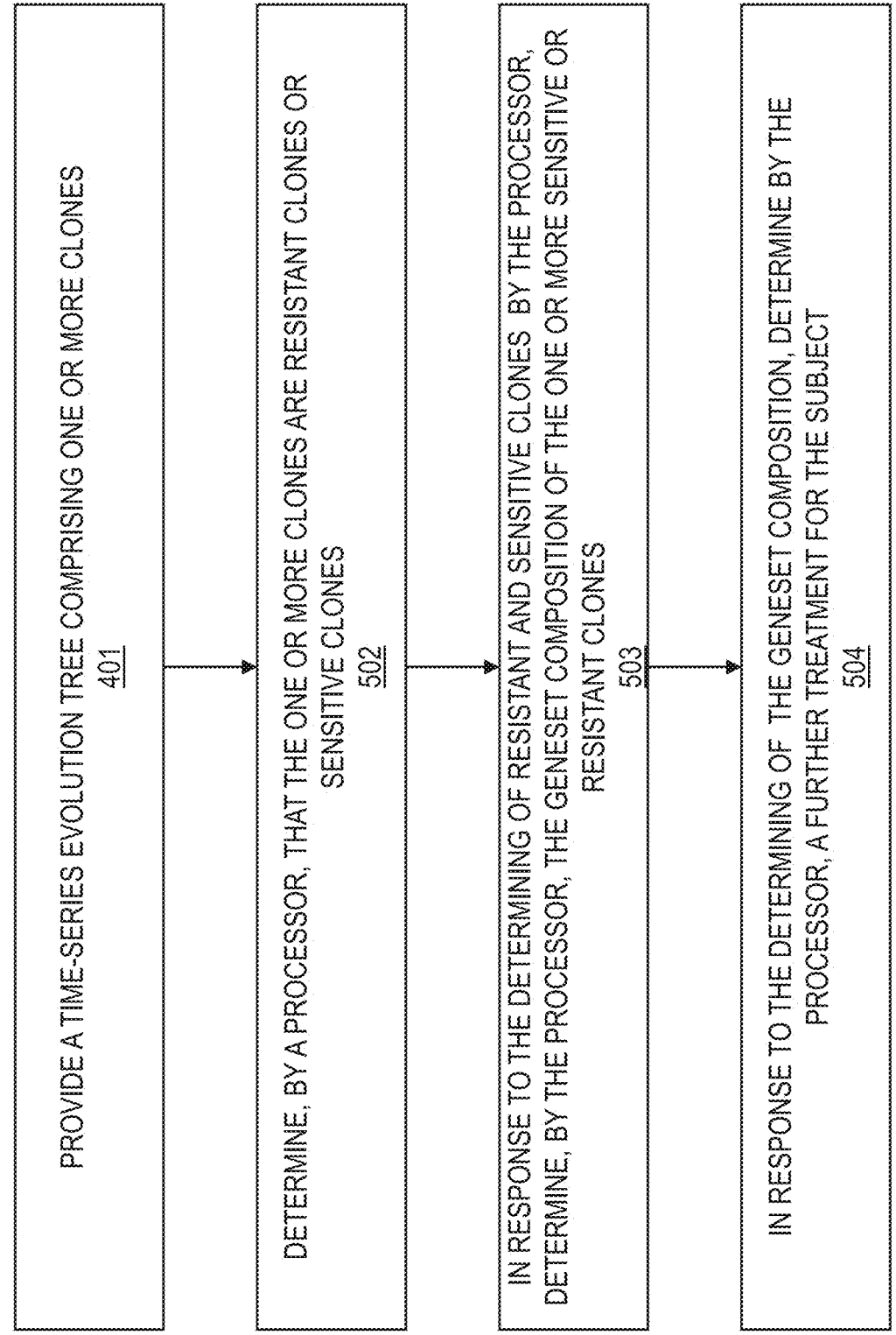
FIG. 5 is a flowchart of a computer-implemented method for determining a cancer treatment according to embodiments of the present invention.

FIG. 5 is a flowchart of a computer-implemented method 400 by computer system 302 for determining a cancer treatment according to embodiments of the present invention. At block 501, a time series evolution tree 100 including one or more clones at each of the plurality of time points, wherein each time point in the time-series evolution tree represents an event in the subject's cancer treatment is provided by the computer system 302. At block 502, it is determined (by the computer system 302) that the one or more clones are sensitive clones or resistant clones, wherein sensitive clones terminate in response to events in the subject's cancer treatment, and resistant clones survive, appear, or divide in response to events in the subject's cancer treatment. At block 503, in response to the determination of the one or more sensitive or resistant clones, the geneset composition of the one or more sensitive or resistant clones is determined by the computer system 302. And at block 504, in response to the determination of the geneset composition, a further treatment for the subject is determined by the computer system 302.

Figure 6:
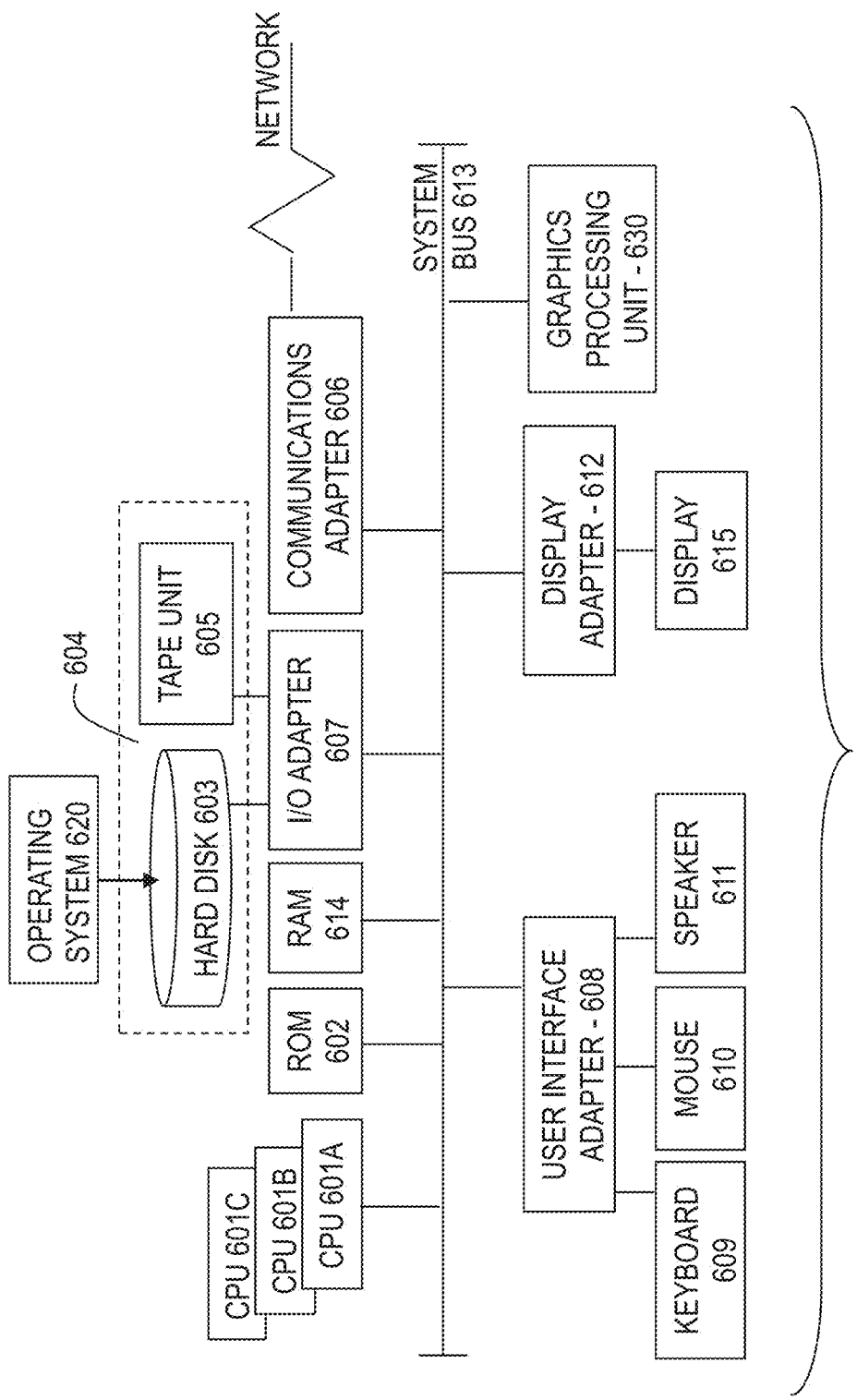
FIG. 6 depicts a computer/processing system having components and/or functionality for practicing one or more embodiments of the present invention.

FIG. 6 depicts exemplary components of a computer system 600 according to one or more embodiments of the present invention. Any of the elements and functionality of computer system 600 can be included in any of the elements in FIGS. 1-5. Particularly, computer system 302 can implement the elements of computer system 600 to perform the functions discussed herein. The computer system 600 is a processing system. The processing system 600 can include one or more central processing units (processors) 601A, 601B, 601C, etc. (collectively or generically referred to as processor(s) 601). In one or more embodiments, each processor 601 can include a reduced instruction set computer (RISC) microprocessor. Processors 601 are coupled to system memory 614 and various other components via a system bus 613. Read only memory (ROM) 602 is coupled to the system bus 613 and can include a basic input/output system (BIOS), which controls certain basic functions of processing system 600.

FIG. 6 further depicts an input/output (I/O) adapter 607 and a network adapter 606 coupled to the system bus 613. I/O adapter 607 can be a small computer system interface (SCSI) adapter that communicates with a hard disk 603 and/or tape storage drive 605 or any other similar component. I/O adapter 607, hard disk 603, and tape storage device 605 are collectively referred to herein as mass storage 604. Operating system 620 for execution on the processing system 600 can be stored in mass storage 604. The network adapter 606 interconnects bus 613 with an outside network, for example, network 540, enabling data processing system 600 to communicate with other such systems. A screen (e.g., a display monitor) 615 is connected to system bus 613 by display adaptor 612, which can include a graphics adapter to improve the performance of graphics intensive applications and a video controller. In one or more embodiments of the present invention, adapters 607, 606, and 612 can be connected to one or more I/O busses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 613 via user interface adapter 608 and display adapter 612. A keyboard 609, mouse 610, and speaker 611 all interconnected to bus 613 via user interface adapter 608, which can include, for example, a Super I/O chip integrating multiple device adapters into a single integrated circuit.

In exemplary embodiments, the processing system 600 includes a graphics processing unit 630. Graphics processing unit 630 is a specialized electronic circuit designed to manipulate and alter memory to accelerate the creation of images in a frame buffer intended for output to a display. In general, graphics processing unit 630 is very efficient at manipulating computer graphics and image processing and has a highly parallel structure that makes it more effective than general-purpose CPUs for algorithms where processing of large blocks of data is done in parallel.

Thus, as configured in FIG. 6, the processing system 600 includes processing capability in the form of processors 601, storage capability including system memory 614 and mass storage 604, input means such as keyboard 609 and mouse 610, and output capability including speaker 611 and display 615. In one implementation, a portion of system memory 614 and mass storage 604 collectively store an operating system coordinate the functions of the various components shown in FIG. 6.

The technical problems solved by the invention include providing a method for automatically inferring the phenotypes that emerge in a time series evolution tree, e.g., an evolutionary birth-death tree. In addition, the invention provides a means of means of determining when a biological pathway becomes functionally relevant in the etiology of cancer. This invention addresses both of these problems to provide targetable pathways for drug intervention or treatment modification by automatically determining the modes of response of a tumor to external perturbations as captured in the subject's clinical history and then identifying when biological pathways become or cease being functionally relevant.

The present invention can be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
responsive to cancer treatment for a tumor of a subject, generating, by a processor, a time-series evolution tree comprising one or more clones at each of the plurality of time points;
determining, by the processor, that the one or more clones are resistant clones that differ from sensitive clones in the time-series evolution tree, wherein the sensitive clones terminate in response to events in the subject's cancer treatment, and the resistant clones survive, appear, or divide in response to events in the subject's cancer treatment, wherein the time-series evolution tree is based on sequence data for the tumor from the subject at a plurality of time points, wherein each time point in the time-series evolution tree represents an event in the subject's cancer treatment, the events corresponding to a first type of the cancer treatment versus a second type of the cancer treatment, and wherein a clone is a collection of gene alterations;
based at least in part on determining that the one or more clones that are the resistant clones, generating, by the processor, a geneset representation comprising a geneset composition of the one or more clones that are the resistant clones;
based at least in part on determining the geneset composition for the resistant clones, previously determined in the time-series evolution tree, that survive, appear, or divide in response to events in the subject's cancer treatment, determining by the processor, a further treatment for the subject; and
administering the further treatment to the subject for the resistant clones, previously determined in the time-series evolution tree, that survive, appear, or divide in response to events in the subject's cancer treatment, wherein the further treatment comprises an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination comprising one or more of the foregoing.

2. The computer-implemented method of claim 1, further comprising administering the further treatment to the subject.

3. The computer-implemented method of claim 1, wherein determining, by the processor, the geneset composition of the one or more clones that are the sensitive or resistant clones, comprises performing, by the processor, a Fisher's exact test on a significance of a size of an intersection between members of a putative geneset and the one or more clones.

4. The computer-implemented method of claim 1, wherein the subject's cancer treatment comprises radiation therapy, surgery, chemotherapy, targeted therapy, hormone therapy, immunotherapy, stem cell transplant, or a combination comprising at least one of the foregoing.

5. The computer-implemented method of claim 1, wherein the further treatment further comprises a signal transduction pathway inhibitor.

6. The computer-implemented method of claim 1, wherein the geneset composition comprises a microtubule inhibition pathway, a DNA repair pathways, or an apoptotosis pathway.

7. The computer-implemented method of claim 1, wherein determining by the processor, a further treatment for the subject, comprises comparing the geneset composition with a database determined from a plurality of tumors from a plurality of subjects.

8. A computer program product for generating a cancer treatment, the computer program product comprising a computer readable storage medium having program instructions embodied therewith, the program instructions executable by a processor to cause the processor to perform operations comprising:
based on sequence data for a tumor from a subject at a plurality of time points, generating, by the processor, a time-series evolution tree, the time-series evolution tree comprising one or more clones at each of the plurality of time points, wherein each time point in the time-series evolution tree represents an event in the subject's cancer treatment, and wherein a clone is a collection of gene alterations;
responsive to cancer treatment for the tumor of the subject, determining, by the processor, that the one or more clones are resistant clones that differ from sensitive clones, wherein the sensitive clones terminate in response to events in the subject's cancer treatment, and the resistant clones survive, appear, or divide in response to events in the subject's cancer treatment, wherein the time-series evolution tree is based on sequence data for the tumor from the subject at a plurality of time points, wherein each time point in the time-series evolution tree represents an event in the subject's cancer treatment, the events corresponding to a first type of the cancer treatment versus a second type of the cancer treatment;
in response to the determination of the one or more clones that are the resistant clones, generating, by the processor, a geneset representation comprising a geneset composition of the one or more clones that are the resistant clones;
in response to the determination of the geneset composition for the resistant clones, previously determined in the time-series evolution tree, that survive, appear, or divide in response to events in the subject's cancer treatment, determining by the processor, a further treatment for the subject; and
administering the further treatment to the subject for the resistant clones, previously determined in the time-series evolution tree, that survive, appear, or divide in response to events in the subject's cancer treatment, wherein the further treatment comprises an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination comprising one or more of the foregoing.

9. The computer program product of claim 8, wherein determining, by the processor, the geneset composition of the one or more clones that are the sensitive or resistant clones, comprises performing, by the processor, a Fisher's exact test on a significance of a size of an intersection between members of a putative geneset and the one or more clones.

10. The computer program product of claim 8, wherein the subject's cancer treatment comprises radiation therapy, surgery, chemotherapy, targeted therapy, hormone therapy, immunotherapy, stem cell transplant, or a combination comprising at least one of the foregoing.

11. The computer program product of claim 8, wherein the further treatment further comprises a signal transduction pathway inhibitor.

12. The computer program product of claim 8, wherein determining by the processor, a further treatment for the subject, comprises comparing the geneset composition with a database determined from a plurality of tumors from a plurality of subjects.

13. The computer program product of claim 8, wherein the geneset composition comprises a microtubule inhibition pathway, a DNA repair pathways, or an apoptosis pathway.

14. A system for cancer treatment comprising:
   a processor; and
   a computer readable storage medium storing comprising executable instructions that, when executed by the processor, cause the processor to perform operations comprising:
      based on sequence data for a tumor from a subject at a plurality of time points, generating, by the processor, a time-series evolution tree, the time-series evolution tree comprising one or more clones at each of the plurality of time points, wherein each time point in the time-series evolution tree represents an event in the subject's cancer treatment, and wherein a clone is a collection of gene alterations;
      responsive to cancer treatment for the tumor of the subject, determining, by the processor, that the one or more clones are resistant clones that differ from sensitive clones, wherein the sensitive clones terminate in response to events in the subject's cancer treatment, and the resistant clones survive, appear, or divide in response to events in the subject's cancer treatment, wherein the time-series evolution tree is based on sequence data for the tumor from the subject at a plurality of time points, wherein each time point in the time-series evolution tree represents an event in the subject's cancer treatment, the events corresponding to a first type of the cancer treatment versus a second type of the cancer treatment;
      in response to the determination of the one or more clones that are the resistant clones, generating, by the processor, a geneset representation comprising a geneset composition of the one or more clones that are the resistant clones;
      in response to the determination of the geneset composition for the resistant clones, previously determined in the time-series evolution tree, that survive, appear, or divide in response to events in the subject's cancer treatment, determining by the processor, a further treatment for the subject; and
      administering the further treatment to the subject for the resistant clones, previously determined in the time-series evolution tree, that survive, appear, or divide in response to events in the subject's cancer treatment, wherein the further treatment comprises an antimetabolite, an antimicrotubule agent, an alkylating agent, a nitrogen mustard, a nitrosourea, a platinum agent, an anthracycline, an antibiotic, a topoisomerase inhibitor, an alkyl sulfonate, a triazine, an ethyenimine, a folic acid analog, a pyrimidine analogue, a purine analog, an antitumor antibiotic, a hormone, an anti-angiogenic agent, an immunotherapeutic agent, a cell cycle signaling inhibitor, or a combination comprising one or more of the foregoing.

15. The system of claim 14, wherein determining, by the processor, the geneset composition of the one or more clones that are the sensitive or resistant clones, comprises performing, by the processor, a Fisher's exact test on a significance of a size of an intersection between members of a putative geneset and the one or more clones.

16. The system of claim 14, wherein the subject's cancer treatment comprises radiation therapy, surgery, chemotherapy, targeted therapy, hormone therapy, immunotherapy, stem cell transplant, or a combination comprising at least one of the foregoing.

17. The system of claim 14, wherein the further treatment further comprises a signal transduction pathway inhibitor.

18. The system of claim 14, wherein determining by the processor, a further treatment for the subject, comprises comparing the geneset composition with a database determined from a plurality of tumors from a plurality of subjects.

19. The system of claim 14, wherein the geneset composition comprises a microtubule inhibition pathway, a DNA repair pathways, or an apoptosis pathway.

* * * * *